United States Patent [19]

Zandkarimi

[11] Patent Number: 5,312,248

[45] Date of Patent: May 17, 1994

[54] BRACKET MARKING GAUGE

[76] Inventor: Farnaz Zandkarimi, 1107 Via Alta, Burbank, Calif. 91501

[21] Appl. No.: 42,641

[22] Filed: Apr. 5, 1993

[51] Int. Cl.⁵ .............................................. A61C 3/00
[52] U.S. Cl. ........................................ 433/3; 433/75; 33/42; 33/514
[58] Field of Search ................... 433/2, 3, 24, 70, 75; 33/42, 514

[56] References Cited

U.S. PATENT DOCUMENTS 1,937,660 12/1933 Luker ........................................ 33/42
2,618,068 11/1952 Apple ...................................... 433/75
3,871,098 3/1975 Dean ........................................ 433/3
5,064,369 11/1991 Kawaguchi ............................. 433/3

Primary Examiner—John J. Wilson
Attorney, Agent, or Firm—J. E. Brunton

[57] ABSTRACT

A disposable marking gauge for use in certain orthodontic procedures to mark a patient's tooth with a readily visible mark at the precise location relative to the occlusal surface of the tooth. The marking is especially useful in locating support wire positioning brackets on the patient's teeth so that they can be bonded to the teeth at precise locations relative to the occlusal surfaces of the teeth.

11 Claims, 2 Drawing Sheets

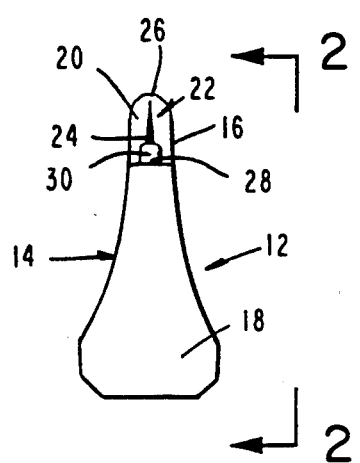
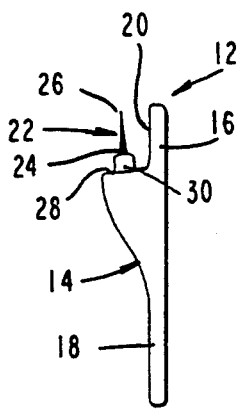
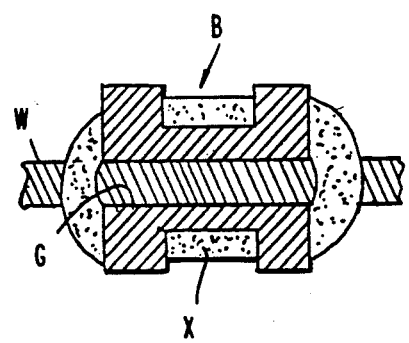
FIG. 1    FIG. 2    FIG. 9
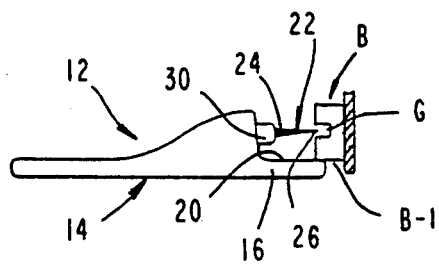
FIG. 10
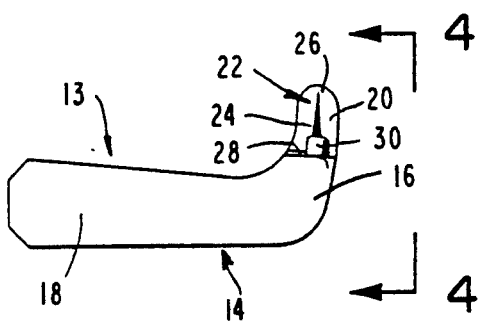
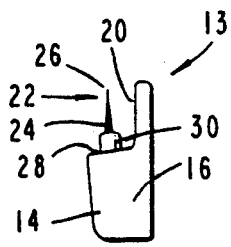
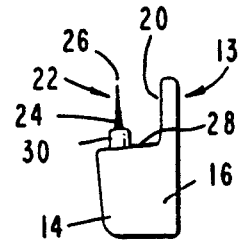
FIG. 3    FIG. 4    FIG. 5

BRACKET MARKING GAUGE

BACKGROUND OF THE INVENTION

1. Field of the Invention

The present invention relates generally to gauges for use in orthodontic procedures. More particularly, the invention concerns a marking gauge for marking a patients teeth to identify the precise locations at which arch wire positioning brackets of the character used in treatment of malocclusion are to be bonded.

2. Discussion of the Invention

A common orthodontic procedure involves the treatment of patients for malocclusion, that is the irregular contact of opposing teeth in the upper and lower jaws. This treatment, sometimes referred to by laypersons as "teeth straightening", typically involves the use of an oral appliance consisting generally of wires or bands used to correct misalignment of the teeth and jaws by exerting controlled pressure on the teeth. The wires or bands are generally held in position by small brackets which are affixed to the front surfaces of the teeth by adhesive bonding. The brackets are usually provided with transverse slots for closely receiving the wire or band. Critical to the success of the procedure is the proper positioning of the brackets relative to the incisal or occlusal surfaces of the teeth.

In the past, several types of positioning instruments for use in placement of the brackets have been suggested. One such instrument, known as the Philips Positioning Instrument facilitates placement of the brackets using a vermier scale that rotates a sighting cursor in relationship with tweezer tips. Another prior are device, called the Boone Bracket Positioning Gauge comprises a generally "X" shaped gauge having a surface that is placed on the occlusal surface of the tooth, and a fixed-pin that scribes the bracket height. Another prior art device called the Dougherty Bracket Positioning Gauge comprises an elongated wire which spans the patient's teeth and functions to mechanically position the brackets on the teeth.

As a general rule, the prior art positioning instruments are relatively complex and quite expensive. Additionally, they tend to be somewhat difficult and time consuming to use. Further, they must be carefully sterilized after each use.

The thrust of the present invention is to overcome the drawbacks of the prior art by providing a simple, easy-to-use, inexpensive and economical, disposable bracket marking gauge for use in locating the arch wire supporting brackets. The device of the present invention includes an integral marking element for marking a line directly on the surface of the tooth can be used by the doctor in precisely locating the bracket on the tooth. Specially configured marking gauges are provided for ease in marking both the front and back teeth. Additionally, different gauges are provided for marking teeth of different length.

SUMMARY OF THE INVENTION

It is an object of the present invention to provide an inexpensive, easy-to-use marking gauge for use in certain orthodontic procedures to mark a patent's tooth with a readily visible mark at the precise location relative to the occlusal surface of the tooth.

Another object of the invention is to provide a marking gauge of the aforementioned character which is especially useful in bonding arch support wire positioning brackets on the patient's teeth at precise locations relative to the occlusal surface. The novel design of the gauges results in substantial savings of clinical time over conventional procedures.

Another object of the invention is to provide marking gauges of the character described which can be used for easy marking of both front and back teeth.

Another object of the invention in to provide marking gauges having marking elements positioned at various distances from a fixed marking surface that is adapted to engage the incisal surface of the tooth.

Still another object of the invention is to provide marking gauges of the type described in the preceding paragraphs that are of simple construction so that they can be inexpensively produced in quantity thereby making it economically feasible to dispose of the devices after use. In this way, spread of contamination can be eliminated without the need for implementing costly and time consuming sterilization procedures.

BRIEF DESCRIPTION OF THE DRAWINGS

FIG. 1 is a top plan view of one form of the marking gauge of the present invention for use in marking the front teeth of the patient.

FIG. 2 is a side elevational view taken along lines 2—2 of FIG. 1.

FIG. 3 is a top plan view of another form of the marking gauge of the invention for marking the back teeth of the patient.

FIG. 4 is a view taken along lines 4—4 of FIG. 3.

FIG. 5 is an end view of another form of the marking gauge of the invention similar to that shown in FIGS. 3 and 4 but showing the marking element at a different height relative to the tooth engage gauge surface.

FIG. 9 is an enlarged plan view of one of the brackets shown in FIG. 8 illustrating the manner in which the restraining wire of the corrective appliance is held in position within the brackets.

FIG. 10 is a diagrammatic view illustrating that the distance between the locating surface of the gauge and the point of the marking element corresponds with the center of the arch wire holding groove in the bracket.

DESCRIPTION OF THE INVENTION

Figure 6:
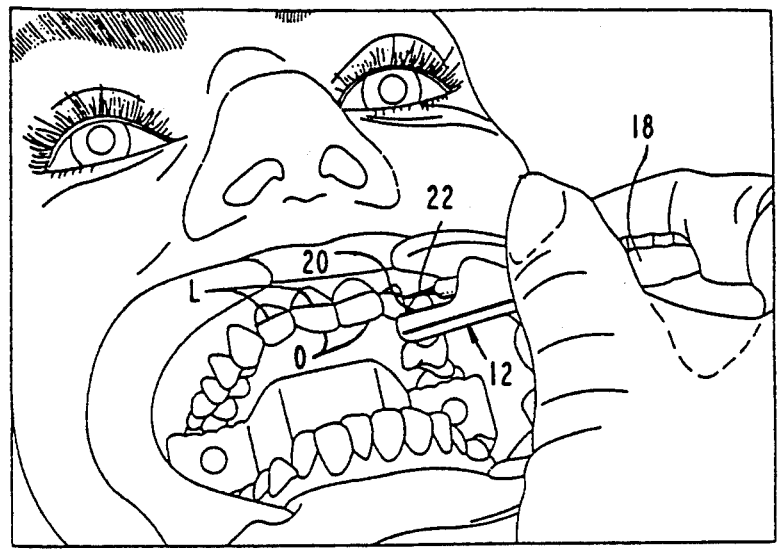
FIG. 6 is a generally diagrammatic view illustrating the use of the embodiment of the invention shown in FIG. 1 for marking the front teeth of the patient.

Referring to the drawings and particularly to FIGS. 1 through 4, one form of the device of the present invention for use in marking the face of a patient's tooth with an easily visible and removable mark is there illustrated. The device illustrated in FIGS. 1 and 2, which is generally designated by the numeral 12, is used in marking the face of the front teeth of the patient in the manner shown in FIG. 6. The embodiment of the invention shown in FIGS. 3 and 4, and generally designated by the numeral 14, is used in marking the face of the back teeth of the patient in the manner generally illustrated in FIG. 7.

Each of the embodiments of the invention comprises a body 14 having a forward portion 16 and an integrally formed handle portion 18. First portion 16 defines a locating surface 20 which is adapted to be placed in engagement with the occlusional surface O of the tooth in the manner best seen in FIG. 6. In the embodiment of the invention shown in FIGS. 1 and 2, the handle portion and the forward portion are aligned. However, in the form of the invention shown in FIGS. 3, 4 and 5, the handle portion conveniently extends angularly with respect to the forward portion 16 to make it easier to use in reaching the back teeth.

Figure 7:
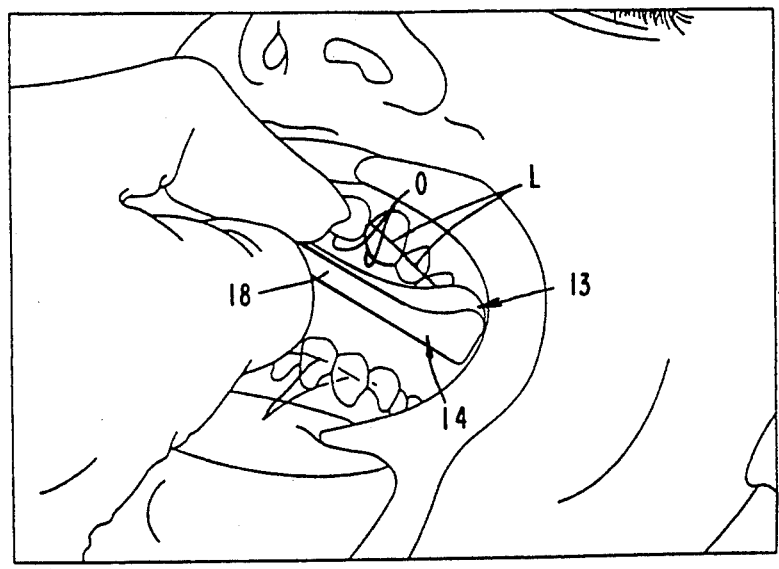
FIG. 7 is a generally diagrammatic view illustrating the use of the embodiment of the invention shown in FIG. 3 for marking the back teeth of the patient.

The forward portion 16 of the marking gauge also includes marking means for marking the surface of the tooth at a fixed distance from the occlusional surface of the tooth in the manner illustrated in FIGS. 6 and 7. In the embodiment of the invention shown in the drawings, the marking means comprises a marking element 22, such as a short length of pencil lead, having a shaft portion 24 and a marking point 26. As indicated in the drawings, shaft 24 extends outwardly from a supporting surface 28 which extends generally perpendicular to locating surface 20. In the instant form of the invention, a socket element 30 is affixed to face 28 and is provided with a central opening within which the marking element can be affixed by adhesive bonding or the like. Socket 30 can be integrally formed with the body portion or can be attached to surface 28 by any suitable means such as adhesive bonding.

As best seen in FIGS. 2 and 4, shaft portion 24 of the marking element 22 extends outwardly from supporting face 28 and is disposed in a spaced apart, generally parallel relationship with locating surface 20. As indicated in FIG. 10, the distance that point 26 is spaced from locating surface 20 corresponds to the distance between the lower surface B-1 of the bracket B and the center of the wire receiving groove G provided in the bracket.

Turning now to FIG. 5, an alternate form of the marking gauge of the invention is there illustrated. This form of the invention is identical to that shown in FIGS. 3 and 4 and previously described herein, save that the distance between marking element 22 and the locating surface 20 is somewhat greater than the distance between the marking element shown in FIG. 4 and the surface 20 of that device. The device of FIG. 5 is used to mark longer teeth such as the patient's eye teeth. It is to be understood that the embodiment of the invention shown in FIGS. 1 and 2 can also be provided with marking elements positioned at varying distances from surface 20 so as to meet the needs of the doctor in marking particular teeth of varying length.

Figure 8:
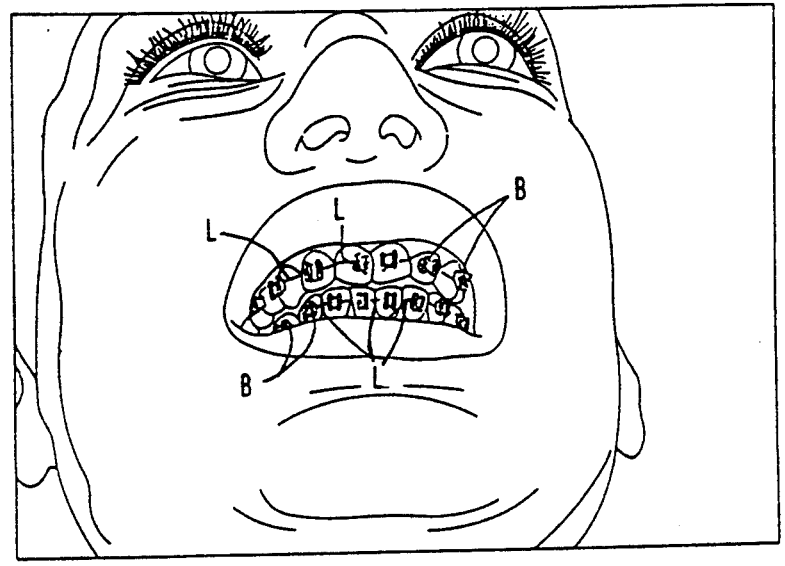
FIG. 8 is a generally diagrammatic view illustrating the emplacement of the wire restraining brackets on the patient's teeth.

Turning to FIG. 8, it is to be noted that after the line L has been appropriately marked on each of the teeth, in the manner illustrated in FIGS. 6 and 7, the arch wire supporting brackets B are precisely affixed to the teeth with the line L in alignment with the center of the groove G provided in the bracket for receiving the arch wire W (see FIG. 10). After the brackets are securely bonded to the face of the teeth, the wire W can be extended over the brackets so that it rests in the groove G in the manner shown in FIG. 9. The wire is held in place within groove G with any appropriate securement means such as the elastomeric band shown in FIG. 9 and designated by the letter X.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A device for use in marking a patient's tooth with an easily visible and removable mark at a precise distance from the occlusal surface of the tooth, comprising a body having a forward portion and a handle portion, said forward portion including:
   (a) a first portion defining a locating surface engagable by the occlusal surface of the tooth, and
   (b) a second portion including marking means for marking the surface of the tooth at a fixed distance from the occlusal surface of the tooth, said marking means comprising a marking element that will inscribe on the surface of the tooth an easily discernible, readily removable mark.

2. A device as defined in claim 1 in which said forward portion and said handle portion are longitudinally aligned.

3. A device as defined in claim 1 in which said marking element includes a body portion and a marking point spaced apart from said locating surface by a first distance, said body portion extending generally parallel to said locating surface.

4. A device as defined in claim 3 in which said marking means comprises a length of marking lead.

5. A device for use in marking the face of a patient's tooth with an easily visibly and removable mark at a precise distance from the occlusal surface of the tooth, comprising a body having a forward portion and integrally formed handle portion, said forward portion including:
   (a) a first portion defining a locating surface adapted to be placed in engagement with the occlusal surface of the tooth; and
   (b) a second portion including a marking element for marking an easily visible, removable line along the surface of the tooth located at a fixed distance from the occlusal surface of the tooth, said marking element having a marking point spaced apart from said locating surface by a first distance.

6. A device as defined in claim 5 in which said handle portion extends generally perpendicular to said forward portion and in which said marking point is spaced apart from said locating surface by a second distance greater than said first distance.

7. A device as defined in claim 5 in which said forward portion includes a supporting surface extending generally perpendicular to said locating surface and in which said marking element includes a shaft portion extending outwardly from said supporting surface in a direction substantially parallel to said locating surface.

8. A device as defined in claim 7 in which said shaft is embedded in a socket member affixed to said supporting surface.

9. A device as defined in claim 8 in which said shaft comprises a marking lead.

10. A device as defined in claim 9 in which said forward portion and said handle portion are constructed from an injection moldable plastic.

11. A device for use in marking a patient's tooth with an easily visible and removable mark at a precise distance from the occlusal surface of the tooth, comprising a body having a forward portion and a handle portion, said handle portion extending at an angle with respect to said forward portion, said forward portion including:
   (a) a first portion defining a locating surface engagable by the occlusal surface of the tooth; and
   (b) a second portion including marking means for marking the surface of the tooth at a fixed distance from the occlusal surface of the tooth.

* * * * *